US00PP34060P2

(12) United States Plant Patent
Griffin

(10) Patent No.: US PP34,060 P2
(45) Date of Patent: Mar. 22, 2022

(54) ***MANGAVE* PLANT NAMED 'TEQUILA FIRE'**

(50) Latin Name: ***Mangave* hybrid**
Varietal Denomination: TEQUILA FIRE

(71) Applicant: Altman Specialty Plants, Inc, Vista, CA (US)

(72) Inventor: Kelly Griffin, Carlsbad, CA (US)

(73) Assignee: Altman Specialty Plants Inc., Vista, CA (US)

( * ) Notice: Subject to any disclaimer, the term of this patent is extended or adjusted under 35 U.S.C. 154(b) by 0 days.

(21) Appl. No.: 17/349,322

(22) Filed: Jun. 16, 2021

(51) Int. Cl.
*A01H 5/02* (2018.01)
*A01H 6/12* (2018.01)

(52) U.S. Cl.
USPC ..... Plt./373
CPC ..... *A01H 6/12* (2018.05)

(58) Field of Classification Search
USPC ..... Plt./373
CPC ..... A01H 6/12
See application file for complete search history.

*Primary Examiner* — Anne Marie Grunberg
(74) *Attorney, Agent, or Firm* — Cassandra Bright

(57) ABSTRACT

A new and distinct cultivar of *Mangave* plant named 'TEQUILA FIRE' is disclosed, characterized by a fiery red and green foliage color. Red foliar coloration increases in density with high light. Foliage is wide, soft and flexible and nearly spineless with no sharp terminal spine. Plants have a moderate growth rate and are slower to flower than other *Mangaves*, resulting in longer lived plants in cultivation. The new variety is an *Mangave*, typically produced as a garden or container plant.

2 Drawing Sheets

Figure 1:
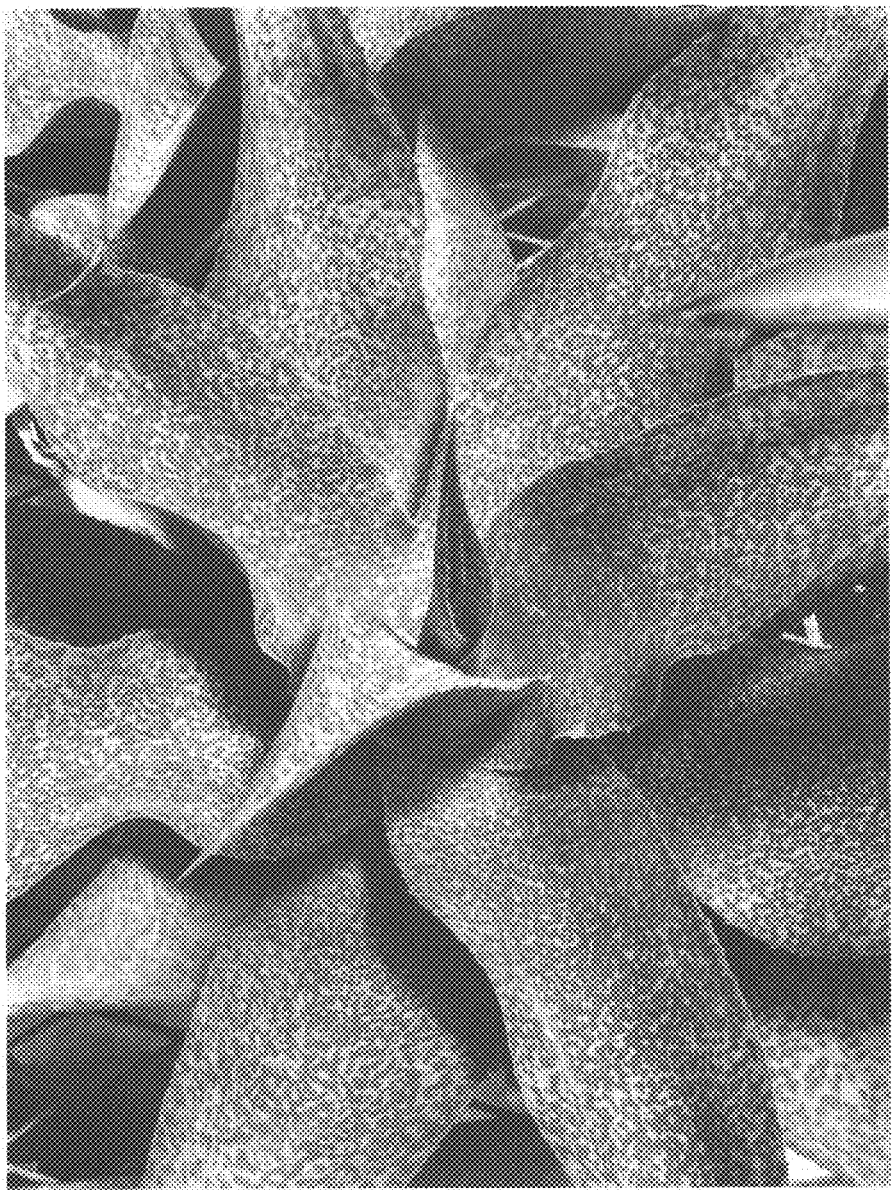

Latin name of the genus and species: *Mangave* hybrid.
Variety denomination: 'TEQUILA FIRE'.

BACKGROUND OF THE INVENTION

The new cultivar is a product of a planned breeding program. The seed parent is a proprietary, unnamed, unpatented *Mangave* hybrid. The pollen parent is a proprietary, unnamed, unpatented *Agave* hybrid. The crossing was made in April of 2016 at a commercial greenhouse in Vista, Calif. 'TEQUILA FIRE' was found and selected by the inventor in June 2017 at a commercial greenhouse in Vista, Calif.

Asexual reproduction of the new cultivar 'TEQUILA FIRE' was first performed by tissue culture at a commercial laboratory in Vista, Calif. in July 2017. 'TEQUILA FIRE' has since produced several generations and has shown that the unique features of this cultivar are stable and reproduced true to type.

SUMMARY OF THE INVENTION

The cultivar 'TEQUILA FIRE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'TEQUILA FIRE'. These characteristics in combination distinguish 'TEQUILA FIRE' as a new and distinct *Mangave* cultivar:

1. Fiery red coloration of leaves especially in full sun.
2. Soft, flexible and nearly spineless leaves. No sharp terminal spine.
3. Moderate growth rate.

4. Slower to flower than other *Mangaves* which translates to longer lived plants in cultivation. Flowering not observed to date.
5. Wide leaves.

PARENTAL COMPARISON

Plants of the new cultivar 'TEQUILA FIRE' are similar to the seed parent in most horticultural characteristics. However, plants of the new variety differ from the seed parent in the following:

1. Plants of the new variety are more compact than plants of the seed parent.
2. The new variety has brighter red foliage than the seed parent, which has subtle burgundy foliage.

Plants of the new cultivar 'TEQUILA FIRE' are similar to the pollen parent in most horticultural characteristics. However, plants of the new variety differ in the following:

1. The seedling has a different leaf color than the pollen parent.
2. The new variety is acualescent and does not form a trunk.

COMMERCIAL COMPARISON

'TEQUILA FIRE' can be compared to the commercial variety *Mangave* 'Mission to Mars', U.S. Plant Pat. No. 29,393. The two *Mangave* varieties are similar in most horticultural characteristics; however, the new variety differs in the following:

1. The new variety has brighter red foliage than this comparator, which has burgundy foliage.
2. The new variety has wider flat leaves as opposed to channeled, cupped leaves this comparator.

3. The new variety has nearly spineless leaves with no sharp terminal spine. This comparator has medium-sized, coarsely dentate margins.

'TEQUILA FIRE' can be compared to the unpatented commercial variety *Agave* 'Blue Flame'. The two varieties are similar in most horticultural characteristics; however, the new variety differs in the following:

1. The new variety has red foliage; this comparator has blue foliage.
2. The new variety is acaulescent and a more compact plant than this comparator.

BRIEF DESCRIPTION OF THE PHOTOGRAPHS

The accompanying photograph in FIG. 1 illustrates in full color a typical plant of 'TEQUILA FIRE' grown with some shade in a greenhouse in Vista, Calif. This plant is approximately about 24 months old, shown in a 2-gallon container.

Figure 2:
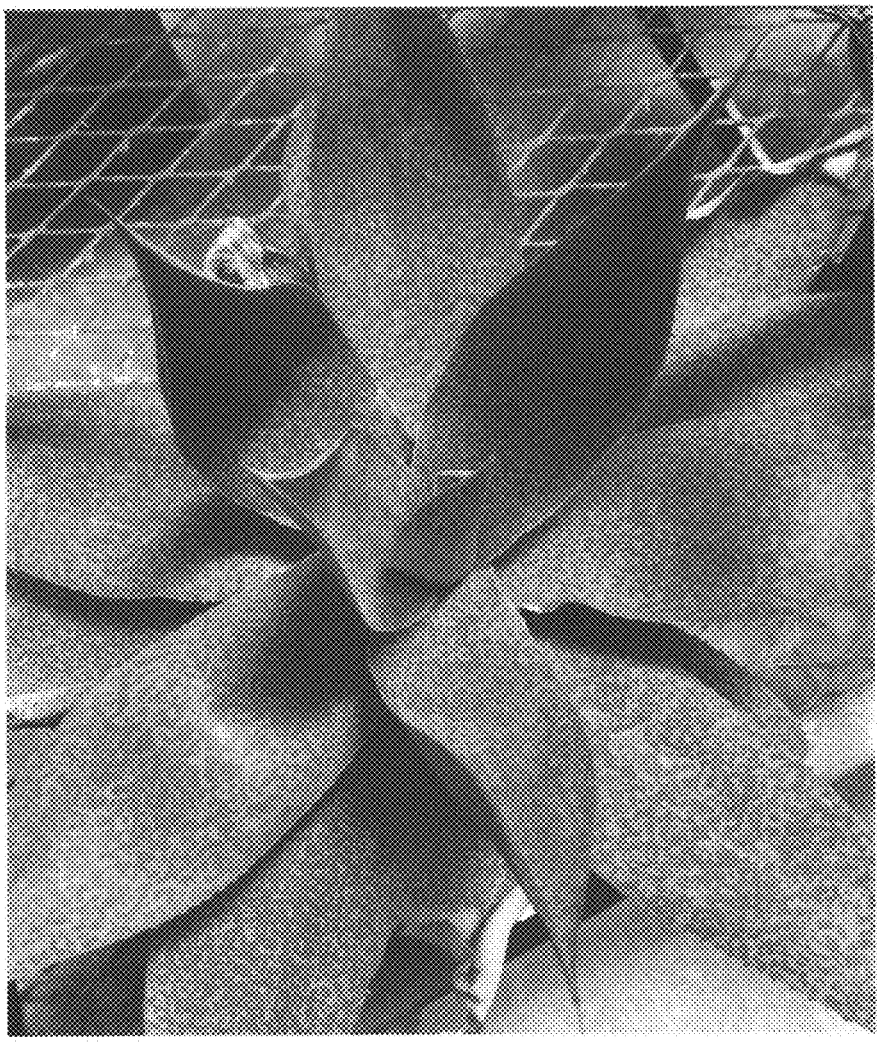

FIG. 2 illustrates in full color a typical plant of 'TEQUILA FIRE' grown in high light, full sun in a greenhouse in Vista, Calif. This plant is approximately about 24 months old, shown in a 2-gallon container.

The photographs were taken using conventional techniques and although colors may appear different from actual colors due to light reflectance are as accurate as possible by conventional photographic techniques.

DETAILED BOTANICAL DESCRIPTION

In the following description, color references are made to The Royal Horticultural Society Color Chart, 2007 edition, except where general terms of ordinary dictionary significance are used. The following observations and measurements describe 'TEQUILA FIRE' plants grown in a commercial greenhouse in Vista, Calif. Temperatures ranged from about 21° C. to 25° C. during the day, and 18° C. to 21° C. during the night. No artificial light, photoperiodic treatments or chemical treatments were given to the plants. Natural light conditions were approximately 2500 to 3000 fc of light. Measurements and numerical values represent averages of typical plant types.

Botanical classification: *Mangave* hybrid 'TEQUILA FIRE'.

Age of the plant described: About 18 months.

PROPAGATION

Root description: Root Description: Thick (4 to 8 mm diameter), dense. Near RHS Yellow-White 158C.

Propagation method: Tissue culture.

PLANT

Growth habit: Succulent herbaceous perennial with basal rosettes of leaves radially arranged and slightly undulating. Central foliage is upright, older, outer foliage becomes more horizontal. Plants are radially-symmetrical. Acaulescent.

Container size: 1 gallon.

Height: Approximately 22 cm.

Plant spread: Approximately 30 cm.

Growth rate: Moderate.

Branching characteristics: No branching.

FOLIAGE

Leaf:

*Arrangement*.—Rosette.

*Average length*.—Average 19-21 cm.

*Average width*.—Average 8 cm at the widest point.

*Shape of blade*.—Broad lanceolate.

*Apex*.—Acuminate with no sharp spine.

*Base*.—Clasping.

*Aspect*.—Upright, reflexed, undulate.

*Margin*.—Slightly serrate, serrations small, about 3 mm tall and about 4 mm wide at base. weakly sharp/firm, spaced 3 to 7 mm apart.

*Texture of top surface*.—Glabrous, smooth.

*Texture of bottom surface*.—Glabrous, smooth.

*Quantity of leaves per plant*.—Average 15.

*Color*.—Young foliage upper side: Near RHS Green 138B and 138C, densely covered with irregularly sized rounded blotches colored near Greyed-Purple 185A and 185B. Blotches about 3 to 7 mm in diameter, densely spaced and overlapping. Red coloration covers about 50% of the leaf blade, with the red coloration densest in the center and base of the leaf. Young foliage under side: Near RHS Green 138B and 138C, densely covered with irregularly sized rounded blotches colored near Greyed-Purple 185A and 185B. Blotches about 3 to 7 mm in diameter, densely spaced and overlapping. Red coloration covers about 50% of the leaf blade, with the red coloration densest in the center and base of the leaf. Mature foliage upper side: Near RHS Green 138B, densely covered with irregularly sized rounded blotches colored near Greyed-Purple 185A and 185B. Blotches about 3 to 7 mm in diameter, densely spaced and overlapping. In higher light conditions the red coloration covers about 90% of the leaf blade. In shadier conditions red coloration covers about 60 to 70% of the leaf blade, with the red coloration densest in the center and base of the leaf. Mature foliage under side: Near RHS Green 138B, densely covered with irregularly sized rounded blotches colored near Greyed-Purple 185A and 185B. Blotches about 3 to 7 mm in diameter, densely spaced and overlapping. In higher light conditions the red coloration covers about 90% of the leaf blade. In shadier conditions red coloration covers about 60 to 70% of the leaf blade, with the red coloration densest in the center and base of the leaf.

*Venation*.—Linear. Color indistinguishable from leaf blade.

FLOWER

Not observed.

REPRODUCTIVE ORGANS

Not observed.

OTHER CHARACTERISTICS

Seeds and fruits: Not observed.

Temperature tolerance: Tolerates temperatures from approximately 0° to at least 35° C. Low temperature improved if plants are kept dry.

Disease/pest resistance: Neither resistance nor susceptibility to normal diseases and pests of *Mangave* observed.

What is claimed is:

1. A new and distinct cultivar of *Mangave* plant named 'TEQUILA FIRE' as herein illustrated and described.

* * * * *